United States Patent
Nielsen

(10) Patent No.: US 7,329,417 B2
(45) Date of Patent: Feb. 12, 2008

(54) MEDICAL DRESSING COMPRISING AN ANTIMICROBIAL SILVER COMPOUND

(75) Inventor: Brian Nielsen, Goerloese (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/451,380

(22) PCT Filed: Feb. 8, 2002

(86) PCT No.: PCT/DK02/00095

§ 371 (c)(1),
(2), (4) Date: Dec. 30, 2003

(87) PCT Pub. No.: WO02/062403

PCT Pub. Date: Aug. 15, 2002

(65) Prior Publication Data

US 2004/0086549 A1    May 6, 2004

(30) Foreign Application Priority Data

Feb. 8, 2001    (DK) .............................. 2001-00202

(51) Int. Cl.
*A61F 13/00* (2006.01)
*A61K 9/70* (2006.01)
*A61L 15/16* (2006.01)
*A61L 15/00* (2006.01)

(52) U.S. Cl. .............. 424/443; 424/445; 424/446; 424/447; 424/448; 424/449

(58) Field of Classification Search ............. 424/443, 424/449, 448
See application file for complete search history.

(56) References Cited

U.S. PATENT DOCUMENTS

| 4,231,369 | A | 11/1980 | Sorensen et al. ........... 128/283 |
| 4,367,732 | A | 1/1983 | Poulsen et al. ............. 128/156 |
| 4,525,410 | A | 6/1985 | Hagiwara et al. |
| 4,655,210 | A * | 4/1987 | Edenbaum et al. ........... 602/46 |
| 5,051,259 | A | 9/1991 | Olsen et al. ................ 424/443 |
| 5,100,671 | A | 3/1992 | Maeda et al. |
| 5,133,821 | A | 7/1992 | Jensen ........................ 156/245 |
| 5,429,819 | A | 7/1995 | Oka et al. |
| 5,441,717 | A * | 8/1995 | Ohsumi et al. ............. 423/306 |
| 5,643,187 | A | 7/1997 | Nastoft et al. ................ 602/43 |
| 5,714,225 | A | 2/1998 | Hansen et al. .............. 428/114 |

(Continued)

FOREIGN PATENT DOCUMENTS

EP    0 264 299    4/1988

(Continued)

OTHER PUBLICATIONS

Milliken & Company: "ALPHASAN", Trademark, Registration date Oct. 3, 2001.*

(Continued)

*Primary Examiner*—Isis Ghali
(74) *Attorney, Agent, or Firm*—Jacobson Holman PLLC

(57) ABSTRACT

A medical dressing comprising a complex of silver and being capable of releasing antimicrobial silver ion activity, the complex comprising silver ion, a transition element of Group IV of the periodic system of elements, cation, phosphate and hydrogen to enable a controlled release of silver ion activity to a wound bed.

25 Claims, 2 Drawing Sheets

U.S. PATENT DOCUMENTS

| | | | |
|---|---|---|---|
| 5,738,860 | A | 4/1998 | Schønfeldt et al. |
| 5,985,301 | A * | 11/1999 | Nakamura et al. .......... 424/404 |
| 6,468,521 | B1 | 10/2002 | Pedersen et al. |
| 6,479,144 | B2 * | 11/2002 | Petrea et al. ................ 428/379 |
| 6,592,888 | B1 * | 7/2003 | Jensen et al. ............... 424/443 |
| 2002/0172709 | A1 | 11/2002 | Nielsen et al. |
| 2002/0187175 | A1 | 12/2002 | Petrea et al. |

FOREIGN PATENT DOCUMENTS

| | | |
|---|---|---|
| EP | 0 272 149 | 6/1988 |
| EP | 0 745 393 A1 | 12/1996 |
| EP | 0 781 566 | 7/1997 |
| EP | 0 905 289 | 3/1999 |
| JP | 03-083905 | 4/1991 |
| JP | 09-078430 | 3/1997 |
| JP | 11-115108 | 4/1999 |
| WO | WO 97/33632 | 9/1997 |
| WO | WO 00/09173 | 2/2000 |
| WO | 00/61367 | 10/2000 |
| WO | 02/36866 | 5/2002 |
| WO | 02/062403 | 8/2002 |
| WO | WO 02/078755 A2 | 10/2002 |

OTHER PUBLICATIONS

"Opinion of the Scientific Committee on Food on the 10$^{th}$ Additional List of Monomers and Additives for Food Contact Materials", European Commission, pp. 1-9, Jul. 11, 2000.

"High Performance Inorganic Materials", Nagoya Research & Development Institute, pp. 1, Oct. 15, 2003.

Milliken & Co., "Alphasan" U.S. Trademark Electronic Search Sys., Oct. 2000, pp. 1-3.

Merck & Co., "The Merck Index", 2001, pp. 1-6.

* cited by examiner

MEDICAL DRESSING COMPRISING AN ANTIMICROBIAL SILVER COMPOUND

This is a nationalization of PCT/DK02/00095 filed Feb. 8, 2002 and published in English.

BACKGROUND OF THE INVENTION

1. Field of the Invention

The present invention relates to a medical dressing comprising a complex of silver and being capable of releasing antimicrobial silver ion activity to a wound, a method for preparing such dressing, and a method for treating a human being.

The antiseptic activity of silver compounds is a well-known property, which has been utilised for many years. The bacteriostatic and fungistatic effect is caused by the silver ion and a simple compound, which has been used clinically, is for instance silver nitrate. Silver nitrate in concentrations of 0.5-1% in water shows disinfectant properties and is used for preventing infections in burns or for prophylaxis of neonatal conjunctivitis. For another silver compound, silver sulfadiazine, the antibacterial effect of the sulfadiazine molecule is further enhanced by the complexing with the disinfecting silver ion. In contrast to the silver nitrate, the solubility of the silver sulfadiazine complex is low and hence, both of the two active parts are only present in solution in low concentrations but may be present over a longer period of time before being washed out at site to be treated. The silver sulfadiazine is intensively used in the treatment of wounds, in particular burns, under the trademarks Silvadene® and Flamazine®. Silver-protein-combinations are yet other antiseptic formulations, which have been used, in low concentrations as eye drops.

2. Description of the Related Art

Antiseptics based on the silver ion are further used in various medical devices. One example of such application is the use in the wound dressing sold by Johnson & Johnson under the trademark Actisorb® which is an activated charcoal cloth dressing. Another example is the wound dressing sold under the trademark EZ-Derm by Genetic Laboratories which dressing is a modified pigskin impregnated with a soluble silver compound intended for treatment of burns.

A number of patents disclose compositions or devices showing antiseptic properties based on contents of silver compounds. EP 272 149 B1 discloses a medical dressing of the 'hydrocolloid' type containing and releasing active components. Silver chloride is a specific antiseptically acting compound mentioned in this patent.

EP patent publication No. 0 905 289 discloses antibacterial cellulose fibre being characterised in that a tertiary amine N-oxide was used as a solvent for pulp, and a silver based antibacterial agent selected from the group of silver zeolite, silver zirconium phosphate, silver calcium phosphate, and silver soluble glass. It is claimed that adding magnetized mineral ore powder may increase the antibacterial effect.

A specific advantage in using the silver ion as antiseptic agent is the general lack of formation of bacterial tolerance to the compound. This is in contrast to many types of antibiotics. However a major drawback when using ionic silver for bacteriostatic purposes is the reduction of the ion to free silver, which results in dark staining.

In the treatment of chronic wounds it is desirable to have a product capable of absorbing wound fluid and, at the same time also releasing antimicrobial activity to the wound bed. Burns, leg ulcers, diabetic foot ulcers and pressure sores may have delayed or slowed healing due to colonisation of the wound bed. For this purpose, it is desirable to have a dressing being able to absorb wound exudates and at the same time releasing antimicrobial activity to the wound, to prevent infection and/or delayed wound healing due to colonisation of the wound.

It is an object of the present invention to provide medical dressings capable of rendering silver ions available sufficiently quickly and in a sufficiently high and lasting concentration to ensure that an effective antiseptic activity is obtained and to ensure that the silver ions will not be released unintendedly from the dressing.

Still further it is an object to provide a method for preparing such medical dressings without losing the antiseptic activity of the silver ions.

Such medical dressings may e.g. be wound dressings, ostomy appliances or dressings for covering sites of the skin having an incision, e.g. for a catheter such as a catheter for drainage purposes.

It has surprisingly been found that certain silver complexes comprising silver and a transitional element of group IV of the Periodic System of Elements may be incorporated in an adhesive or foam matrix of a medical dressing without loosing the antiseptic activity and that the release of silver ions may be controlled to ensure that silver ions will not be released from the dressing unintendedly and that the release may be initiated in a controlled manner.

SUMMARY OF THE INVENTION

The present invention relates to a medical dressing comprising a complex of silver and being capable of releasing antimicrobial silver ion to e.g. a wound bed.

Furthermore, the invention relates to a method for preparing medical dressings in the form of foam being capable of releasing antibacterial activity to a wound bed.

BRIEF DESCRIPTION OF THE DRAWINGS

The invention is disclosed more in detail with reference to the drawings in which.

DETAILED DESCRIPTION OF THE PRESENT INVENTION

Figure 1:
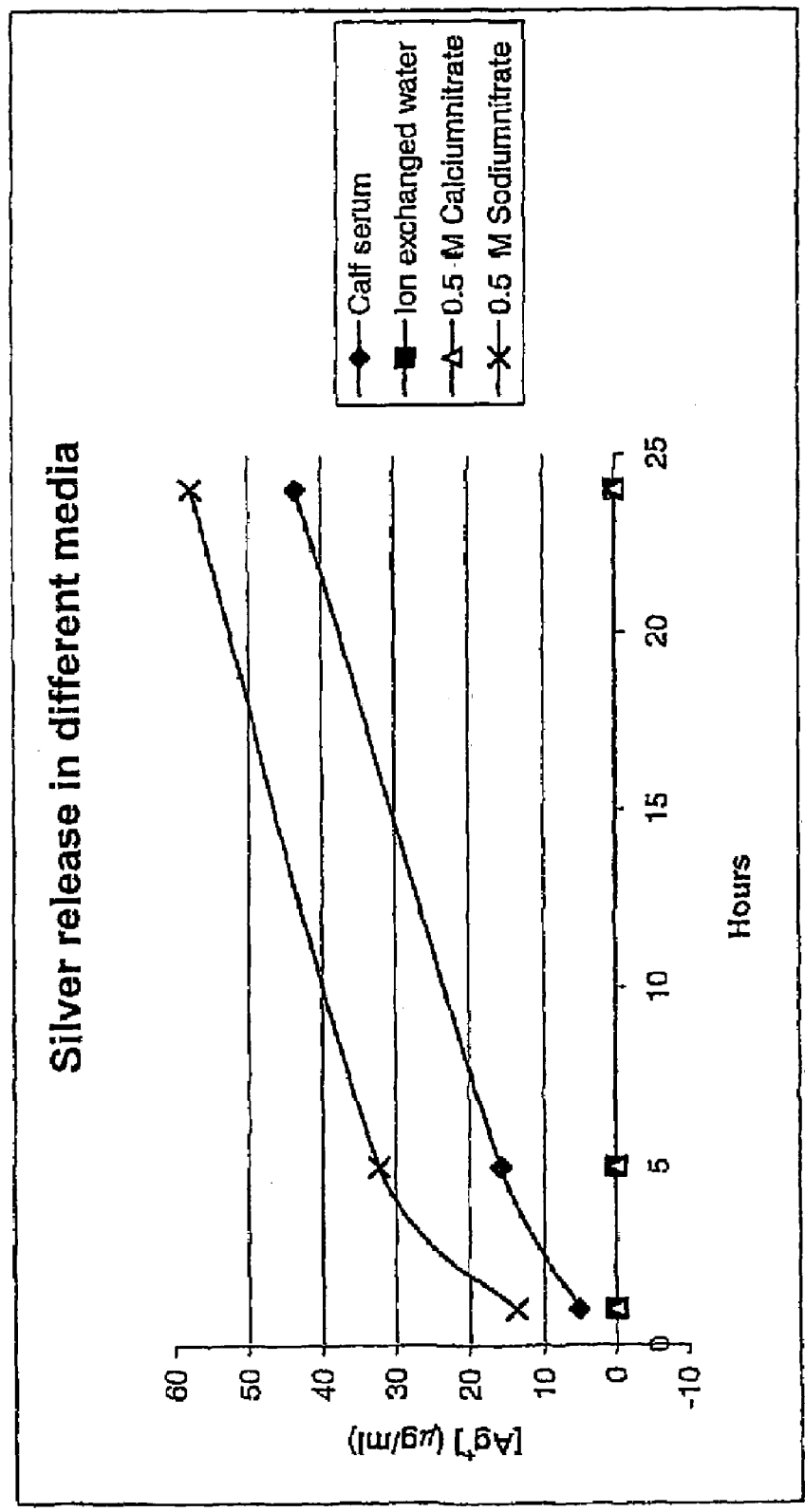
FIG. 1 shows a graphical representation of the release of silver in different media from a dressing according to the invention.

The present invention relates to a medical dressing comprising a complex of silver and being capable of releasing antimicrobial silver ion activity, said complex comprising silver and a transitional element of Group IV of the Periodic System of Elements.

It has been found that silver is only released from a dressing according to the invention, when the dressing is contacted with a liquid comprising ions and no release is seen when contacted with distilled water. This effect is especially pronounced in connection with liquids predominantly comprising monovalent ions.

This finding enables a controlled release of the silver ion activity in that it is not released when a dressing is contacted with distilled water, only on contact with an ionic solution. Thus, it is possible to rinse e.g. a wound or a stoma or the peristomal area of the skin of an ostomate or the area around an incision for e.g. drainage purposes using distilled water without risk of unintended early release of silver ion activity before it is actually needed, namely when e.g. an exudate is present. Furthermore, silver ion activity is not released from parts of a dressing not being wetted by an ionic solution. Still further, distilled water or essentially ion-free water may be used in the production and/or be incorporated in a product of the invention without releasing the silver ion activity.

Without limiting the invention to any specific theory it is assumed that an absorbent medical dressing is capable of absorbing exudate or the like whereafter ion exchange with cations from the absorbed fluid in the dressing releases the silver promoting antimicrobial activity. Thus, it is assumed that when e.g. wound exudate is absorbed into a wound dressing according to the invention, an ion exchange between sodium ions of the exudate and silver of the antimicrobial complex is initiated, and the released silver ions will be transported into the wound bed to exercise antimicrobial activity.

The complex used in accordance with the present invention may preferably comprise a transitional element such as titanium, zirconium or hafnium, and it is especially preferred that the silver is in the form of complex with zirconium.

The complex is suitably a phosphate complex not having adverse effect when in contact with open wounds. Such complex preferably also comprises a further cation such as an alkali metal ion e.g. lithium, sodium, or potassium, preferably sodium.

A silver sodium hydrogen zirconium phosphate complex has proven to be especially suitable for the purpose of the present invention.

The dressings of the invention may have a content of silver in the range of 0.01 to 30 mg silver/$cm^2$ wound dressing. The content of silver is preferably in the range of 0.1 to 15 mg, more preferred in the range of 0.2 to 6 mg, e.g. about 1 mg silver/$cm^2$.

It is preferred that a dressing of the invention comprises an absorbing constituent or element and that the complex of silver is comprised in such absorbing constituent or element as a wound exudate or other liquid will then more easy come into contact with each other.

An absorbing constituent or element may preferably be a separate element of an absorbing foam, a hydrogel, or paste, or be in the form of hydrocolloids and/or an alginate in the form of a separate element or particulate and homogeneously distributed in the dressing. In case of a hydrogel, care must be taken during production that no ionic constituents are used in order not to release the silver ion activity from the complex of silver. Such hydrogels may thus comprise non-ionic absorbers such as non-ionic cellulose derivatives, e.g. hydroxyethyl cellulose or PVP and non-ionic water and optionally non-ionic preservatives such as propylene glycol.

It has been found suitable that the absorption of a medical dressing of the invention is higher than 3 grams per gram wound dressing, preferably higher than 5 grams per gram wound dressing.

In a preferred embodiment of the invention, the dressing comprises a polyurethane foam layer forming at least a part of the skin-contacting surface of the dressing. Such a foam may be produced incorporating particles of a complex comprising silver and a transitional element of Group IV of the Periodic System of Elements homogeneously distributed in the foam without loosing the desired properties.

Such an absorbing element may in one embodiment constitute a dressing of the invention. In such case, the absorbing element may in itself show adhesive properties or it may not show adhesive properties and it will then typically be secured to the desired site using conventional means such as a cover dressing.

In a preferred embodiment of the invention, the dressing comprises a skin-contacting surface comprising an area showing a skin friendly adhesive.

Such a dressing may suitably be a dressing comprising a substantially water-impervious layer or film and a skin-friendly adhesive in which an absorbing constituent or element is incorporated.

The skin-friendly adhesive may be any skin-friendly adhesive known per se, e.g. an adhesive comprising hydrocolloids or other moisture absorbing constituents such as the adhesives disclosed in U.S. Pat. No. 4,231,369 and in U.S. Pat. No. 4,367,732 comprising hydrocolloids. A dressing comprising a separate absorbing element may e.g. be of the type disclosed in U.S. Pat. No. 5,051,259 or U.S. Pat. No. 5,714,225.

A water impervious layer or film may be of any suitable material known per se for use in the preparation of wound dressings e.g. a foam, a non-woven layer or a polyurethane, polyethylene, polyester or polyamide film. A suitable material for use as a water impervious film is a polyurethane film such as the low friction film material is disclosed in U.S. Pat. No. 5,643,187.

A dressing of the invention preferably has bevelled edges in order to reduce the risk of "rolling-up" the edge of the dressing reducing the wear-time. A bevelling may be carried out discontinuously or continuously in a manner known per se e.g. as disclosed in EP patent No. 0 264 299 or in U.S. Pat. No. 5,133,821.

The adhesive may be covered by a protective cover or release liner such as siliconized paper. The protective cover is not present during the use of a dressing of the invention and is therefore not an essential part of the invention.

The dressing of the invention has mainly been described with reference to wound dressings but it will be evident for the skilled in the art that the invention is not limited to wound dressings. Thus, a medical dressing of the invention may be in the form of a wound dressing or an ostomy appliance or a dressing for covering an incision site in the skin.

The invention further relates to a method for preparing a medical dressing in the form of a foam comprising a complex of silver and a transitional element of Group IV of the periodic system of elements which method comprises mixing the complex of silver and an element of transition Group IV of the periodic system of elements with water and a surfactant, adding one or more prepolymer(s) during mixing, transforming the resulting mixture into thin layer having a predetermined thickness, letting the resulting mixture foam and drying the resulting sheet at an elevated temperature. It is contemplated that such a foam system may also be produced directly from isocyanate and polyol(s).

Still further, the invention relates to a method of absorbing exudate from a wound or from an artificial orifice or opening such as the end of an intestine or stoma protruding from the skin of a human body or the skin around a stoma or the area around an incision point for drainage and which method comprises a) identifying the wound, stoma, fistula or drainage site of the patient, b) securing a medical dressing comprising a complex of silver and being capable of releasing antimicrobial silver ion activity, said complex comprising silver and a transitional element of Group IV of the periodic system of elements to the patient's skin in such a manner that covers the area of a wound or surrounds the area of the stoma, the fistula or the drainage site.

DESCRIPTION OF THE PREFERRED EMBODIMENTS

The invention is now explained more in detail with reference to the below working Example which discloses preferred embodiments of the invention and which is not to be considered as limiting the scope of the protection set forth in the appended claims.

MATERIALS AND METHODS

Newborn Calf Serum, Gibco BRL (Lot. No.: 3033873D)
Sodium nitrate, Merck, analytical grade (Lot. No.: 259337-120)
Calcium Nitrate tetra hydrate, Merck, analytical grade (Lot. No.: 93252-647)
Ion exchanged water (Conductivity 0.04 µS) from internal laboratory supply
Silver nitrate standard 1000 mg/ml, KEBO lab. (Lot. No.: 19797.0500)
Hypol 2002 polyurethane prepolymer, Dow Chemicals
Pluronic 6200 PO-PE block copolymer, BASF
Silver Sodium Hydrogen Zirconium Phosphate available under the Trade name AlphaSan®, Milliken Chemicals
Acticoat Seven, a silver containing wound dressing from Westaim Biomedicals™ Atomic absorption spectrophotometer (Perkin Elmer 305)
A 0.5M sodium nitrate solution was prepared by dissolving 42.49 grams of sodium nitrate in one litre of ion exchanged water during stirring.
A 0.5M calcium nitrate solution was prepared by dissolving 87.07 grams of sodium nitrate in one litre of ion exchanged water during stirring.

Method for Measuring the Release of Silver:

The release of silver was determined by the following method.

Step A) Samples of the material to be tested were punched out in the form of discs having a diameter of 30 mm.

Step B) The sample was immersed in 50 ml of each of the test solutions and stirring was started ($T_0$).

Step C) After stirring for 1, 5, and 24 hours, respectively, 5.0 milliliters of release medium was sampled and replaced with 5.0 milliliters of fresh medium.

Step D) Each sample was analysed using an atomic absorption spectrophotometer and the content of Silver was calculated and presented as a plot as a function of time. Each experiment was carried out in triplicate.

EXAMPLE

Preparation of Antibacterial Foam Product According to the Invention.

A polyurethane foam sheet was produced by mixing Hypol 2002 (20 grams), Pluronic 6200 (0.2 grams), water (20 grams), silver sodium hydrogen zirconium phosphate (3 grams) by first mixing the water, silver compound and Pluronic and then adding this mixture to the Hypol during mixing. While the mixture still was fluid it was transformed into thin layer by pouring the mixture onto a glass plate, placing a siliconised release paper on the mixture and adjusting the thickness to 2 mm using guiding bars and a doctor roll, allowing the mixture to foam for several minutes. When the material was foamed, the foam sheet was dried in a dry air oven at 130° C. The final foamed sheet had a thickness of 4.5 mm and a content of silver of 9200 mg per square meter of foam (0.92 mg silver/cm²).

The release of silver from the product when contacted with different solutions was determined as milligrammes of silver released. The results are presented in the below Table 1 and in FIG. 1.

TABLE 1

| Release Medium | Concentration (µg/ml) | | |
|---|---|---|---|
| | 1 hour | 5 hours | 24 hours |
| Newborn calf serum | 5.22 | 15.74 | 43.38 |
| Ion exchanged water | 0 | 0 | 0 |
| Calcium nitrate | 0 | 0 | 0 |
| Sodium nitrate | 13.76 | 32.24 | 57.64 |

As appears from Table 1 and FIG. 1, no silver was released when in contact with ion exchanged water or calcium nitrate solution whereas a rapid release of silver ions takes place when in contact with monovalent cationic solutions. The highest release of silver was seen when in contact with 0.5M sodium nitrate solution and newborn calf serum which media both contain monovalent cations.

COMPARATIVE EXAMPLE

The release of silver from Acticoat Seven was determined using the same procedure as above and the results are presented in the below Table 2 and in FIG. 2.

TABLE 2

| Release medium | Concentration (µg/ml) | | |
|---|---|---|---|
| | 1 hour | 5 hours | 24 hours |
| Newborn calf serum | 9.75 | 25.04 | 38.81 |
| Ion exchanged water | 12.29 | 28.75 | 51.83 |
| Calcium nitrate | 35.63 | 67.43 | 75.99 |
| Sodium nitrate | 21.45 | 44.18 | 61.39 |

Figure 2:
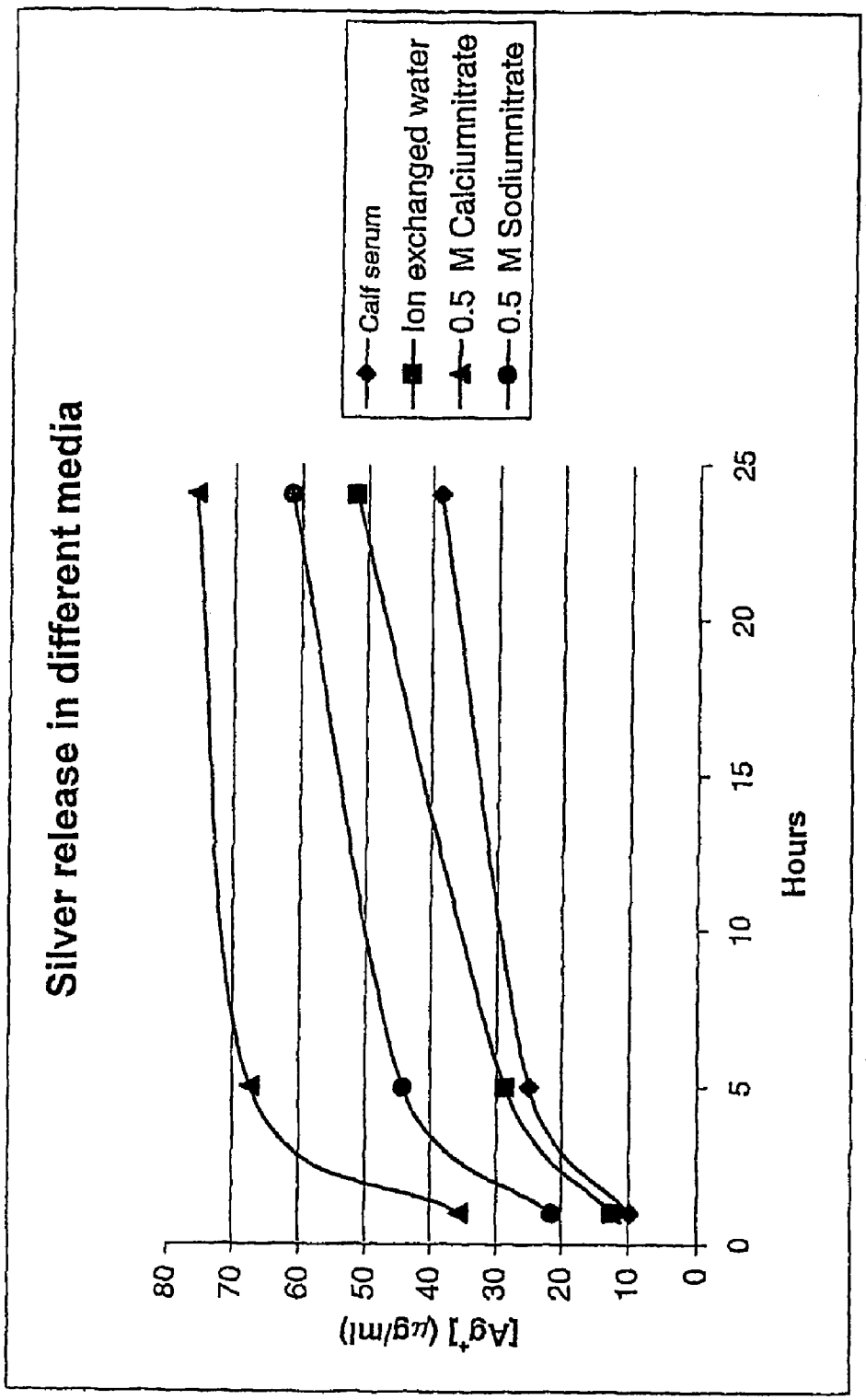
FIG. 2 shows a graphical representation of the release of silver in different media from a dressing of the state of the art comprising silver.

As appears from Table 2 and FIG. 2, silver is released in ion-exchanged water, calcium nitrate solution, sodium nitrate solution, and in newborn calf serum.

Thus, the foam of the invention is superior to the known product with respect to controlling the release of silver ions in that no activity is released when contacted with ion exchanged water whereas a much higher release is observed when in contact with monovalent cations which are e.g. present in new-born calf serum.

The invention claimed is:
1. A medical dressing comprising:
   a) an antimicrobial complex consisting essentially of:
      1) silver ion;
      2) a transitional element of Group IV of the Periodic System of Elements selected from the group consisting of zirconium, titanium and hafnium;
      3) at least one cation selected from the group consisting of lithium, sodium and potassium;
      4) phosphate; and
      5) hydrogen;
   b) at least one absorbing element selected from the group consisting of an absorbing foam; said absorbing element being a separate element in said dressing;
   c) said antimicrobial complex being mixed within said absorbing element such that the concentration of silver ion is between about 0.01 to 30 mg silver/cm² wound dressing;
   d) wherein the silver ion in said antimicrobial complex mixed within said absorbing element, is only capable of being released from said absorbing element when placed in contact with wound exudate or fluid containing monovalent cations; and e) and wherein the silver ion is released in an effective amount to exhibit antiseptic activity in a wound when placed in contact with a wound secreting exudate or fluid containing monovalent cations.

2. A medical dressing as claimed in claim 1, wherein the silver ion is in the form of complex with zirconium.

3. A medical dressing as claimed in claim 2, wherein the silver ion is in the form of a silver sodium hydrogen zirconium phosphate complex.

4. A medical dressing as claimed in claim 1, wherein said dressing comprises a polyurethane foam layer forming at least a part of the skin contacting surface of the dressing.

5. A medical dressing as claimed in claim 1, wherein the skin contacting surface comprises an area having a skin friendly adhesive.

6. A medical dressing as claimed in claim 1, wherein said dressing is in the form of a wound dressing or an ostomy appliance or a dressing for covering an incision site in the skin.

7. A method of absorbing exudate from a wound or from an artificial orifice or opening and treating the same with silver ions, which method comprises the steps of:
a) identifying the wound, artificial orifice or opening of the patient; and
b) securing a medical dressing comprising the dressing of claim 1 in such a manner that said dressing covers the area of a wound or surrounds the area of the artificial orifice or opening.

8. The method of absorbing exudate of claim 7, wherein said artificial orifice or opening is the end of an intestine or stoma protruding from the skin of a human body, or the skin around a stoma, or the area around an incision point for drainage.

9. A medical dressing comprising:
a) an antimicrobial complex consisting essentially of:
1) silver ion;
2) a transitional element of Group IV of the Periodic System of Elements selected from the group consisting of zirconium, titanium and hafnium;
3) at least one cation selected from the group consisting of lithium, sodium and potassium; and
4) phosphate; and
5) hydrogen;
b) at least one absorbing element consisting of alginates, and said absorbing element being homogeneously distributed in the dressing;
c) said antimicrobial complex being mixed within said absorbing element such that the concentration of silver ion is between about 0.01 to 30 rag silver/cm$^2$ wound dressing;
d) wherein the silver ion in said antimicrobial complex mixed within said absorbing element is only capable of being released from said absorbing element when placed in contact with wound exudate or fluid containing monovalent cations; and
e) wherein the silver ion is released in an effective amount to exhibit antiseptic activity in a wound when placed in contact with a wound secreting exudate or fluid containing monovalent cations.

10. A medical dressing as claimed in claim 9, wherein the silver ion is in the form of complex with zirconium.

11. A medical dressing as claimed in claim 10, wherein the silver ion is in the form of a silver sodium hydrogen zirconium phosphate complex.

12. A medical dressing as claimed in claim 9, wherein said dressing comprises a polyurethane foam layer forming at least a part of the skin contacting surface of the dressing.

13. A medical dressing as claimed in claim 9, wherein the skin contacting surface comprises an area having a skin friendly adhesive.

14. A medical dressing as claimed in claim 9, wherein said dressing is in the form of a wound dressing or an ostomy appliance or a dressing for covering an incision site in the skin.

15. A methods of absorbing exudate from a wound or from an artificial orifice or opening and treating the same with silver ions, which method comprises the steps of:
a) identifying the wound, artificial orifice or opening of the patient; and
b) securing a medical dressing comprising the dressing of claim 9 in such a manner that said dressing covers the area of a wound or surrounds the area of the artificial orifice or opening.

16. The method of absorbing exudates of claim 15, wherein said artificial orifice or opening is the end of an intestine or stoma protruding from the skin of a human body, or the skin around a stoma, or the area around an incision point for drainage.

17. A medical dressing comprising:
a) an antimicrobial complex consisting essentially of:
1) silver ion;
2) a transitional element of Group IV of the Periodic System of Elements selected from the group consisting of zirconium, titanium and hafnium;
3) at least one cation selected from the group consisting of lithium, sodium and potassium;
4) phosphate; and
5) hydrogen;
b) at least one absorbing element consisting of alginates, said absorbing element being a separate element in said dressing;
c) said antimicrobial complex being mixed within said absorbing element such that the concentration of silver ion is between about 0.01 to 30 mg silver/cm$^2$ wound dressing;
d) wherein the silver ion in said antimicrobial complex mixed within said absorbing element is only capable of being released from said absorbing element when placed in contact with wound exudate or fluid containing monovalent cations; and
e) wherein the silver ion is released in an effective amount to exhibit antiseptic activity in a wound when placed in contact with a wound secreting exudate or fluid containing monovalent cations.

18. A medical dressing as claimed in claim 17, wherein the silver ion is in the form of complex with zirconium.

19. A medical dressing as claimed in claim 18, wherein the silver ion is in the form of a silver sodium hydrogen zirconium phosphate complex.

20. A medical dressing as claimed in claim 17, wherein said dressing comprises a polyurethane foam layer forming at least a part of the skin contacting surface of the dressing.

21. A medical dressing as claimed in claim 17, wherein the skin contacting surface comprises an area having a skin friendly adhesive.

22. A medical dressing as claimed in claim 17, wherein said dressing is in the form of a wound dressing or an ostomy appliance or a dressing for covering an incision site in the skin.

23. A method of absorbing exudate from a wound or from an artificial orifice or opening and treating the same with silver ions, which method comprises the steps of:
  a) identifying the wound, artificial orifice or opening of the patient; and
  b) securing a medical dressing comprising the dressing of claim 17 in such a manner that said dressing covers the area of a wound or surrounds the area of the artificial orifice or opening.

24. The method of absorbing exudates of claim 23, wherein said artificial orifice or opening is the end of an intestine or stoma protruding from the skin of a human body, or the skin around a stoma, or the area around an incision point for drainage.

25. A medical dressing as claimed in claim 1, wherein the absorbing foam is polyurethane foam.

* * * * *